(12) United States Patent
Bangert

(10) Patent No.: US 8,143,073 B2
(45) Date of Patent: Mar. 27, 2012

(54) APPARATUS FOR CARRYING OUT AN ANALYSIS PROCESS, IN PARTICULAR FOR IDENTIFICATION OF BIOCHEMICAL MOLECULES, AND ANALYSIS PROCESSES WHICH CAN BE CARRIED OUT USING THIS APPARATUS

(75) Inventor: Joachim Bangert, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 540 days.

(21) Appl. No.: 11/502,412

(22) Filed: Aug. 11, 2006

(65) Prior Publication Data

US 2007/0042506 A1    Feb. 22, 2007

(30) Foreign Application Priority Data

Aug. 12, 2005   (DE) .......................... 10 2005 038 239

(51) Int. Cl.
  *G01N 27/00*   (2006.01)
  *G01N 27/06*   (2006.01)
  *G01N 27/08*   (2006.01)
  *G01N 33/00*   (2006.01)
  *G01N 33/553*  (2006.01)

(52) U.S. Cl. ......... 436/526; 436/149; 422/68.1; 422/81; 422/82; 422/82.01; 422/82.02; 422/102; 422/103; 422/104

(58) Field of Classification Search .................. None
See application file for complete search history.

(56) References Cited

U.S. PATENT DOCUMENTS

| 4,280,096 A | 7/1981 | Karthe et al. |
| 4,690,130 A * | 9/1987 | Mirell ................................ 600/2 |
| 5,235,276 A * | 8/1993 | Lew ............................... 324/306 |
| 5,445,970 A | 8/1995 | Rohr |
| 5,981,297 A | 11/1999 | Baselt |
| 6,180,418 B1 | 1/2001 | Lee |
| 6,516,276 B1 * | 2/2003 | Ghandour et al. ............... 702/27 |
| 2001/0052770 A1 * | 12/2001 | Simmonds et al. ........... 324/204 |

(Continued)

FOREIGN PATENT DOCUMENTS

DE    100 50 029 A1    5/2002

(Continued)

OTHER PUBLICATIONS

Tamanaha et al., "Hybrid macro-micro fluidics system for chip-based biosensor," J. Micromech. Microeng., 2002, vol. 12, pp. N7-N17.*

(Continued)

*Primary Examiner* — Unsu Jung
(74) *Attorney, Agent, or Firm* — Harness, Dickey & Pierce, P.L.C.

(57) ABSTRACT

An apparatus is disclosed for carrying out an analysis process, in which probe molecules which are immobilized on a substrate within an analysis area are brought into contact with an analyte solution, which contains target molecules as reaction partners, and reaction events are detected between target molecules and probe molecules with the aid of magnetic marker particles which are coupled to the target molecules or to the probe molecules. An inhomogeneous magnetic field is applied to the analysis area before and/or after detection. In the apparatus, magnetic-field devices are provided at least for the production of an inhomogeneous magnetic field acting in the analysis area, with these magnetic-field devices being part of sequence control for determination of the bonding forces of the reaction events.

19 Claims, 7 Drawing Sheets

U.S. PATENT DOCUMENTS

| | | | |
|---|---|---|---|
| 2002/0119470 A1* | 8/2002 | Nerenberg et al. | 435/6 |
| 2004/0033627 A1* | 2/2004 | Aytur et al. | 436/526 |
| 2004/0219695 A1 | 11/2004 | Fox | |
| 2005/0087000 A1 | 4/2005 | Coehoorn et al. | |
| 2005/0106758 A1 | 5/2005 | Fukumoto et al. | |

FOREIGN PATENT DOCUMENTS

| | | |
|---|---|---|
| DE | 10 2004 039 420 A1 | 2/2006 |
| EP | 1 469 311 A1 | 10/2004 |
| WO | WO 00/61803 A1 | 10/2000 |
| WO | WO 02/29430 A1 | 4/2002 |
| WO | WO 02088696 A1 * | 11/2002 |

OTHER PUBLICATIONS

Giancoli, "Physics for Scientists and Engineers with Modern Physics," $2^{nd}$ Edition, Prentice Hall, Englewood Cliffs, NJ, 1989, pp. 654-656.*

German Office Action dated Feb. 20, 2008 for counterpart German Application.

D.R. Baselt; G. U. Lee; R. J. Colton: Biosensor based on force microscope technology, Journal of Vacuum Science and Technology B, 1996, vol. 14, Bd. 2, S. 789-793.

* cited by examiner

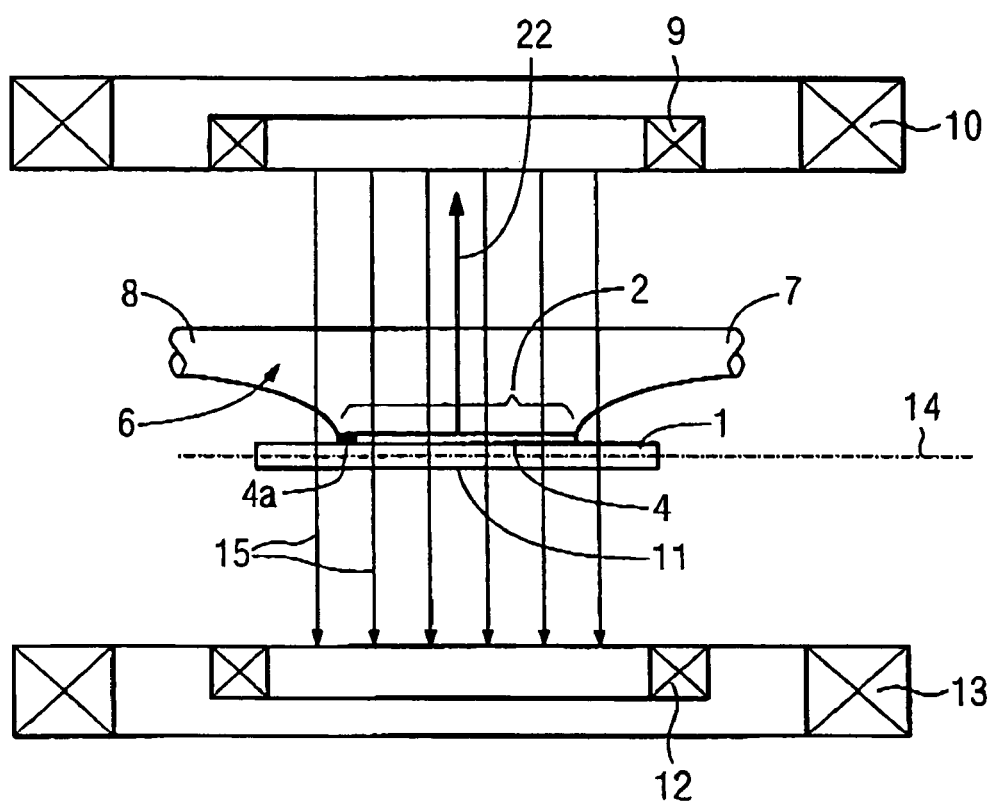

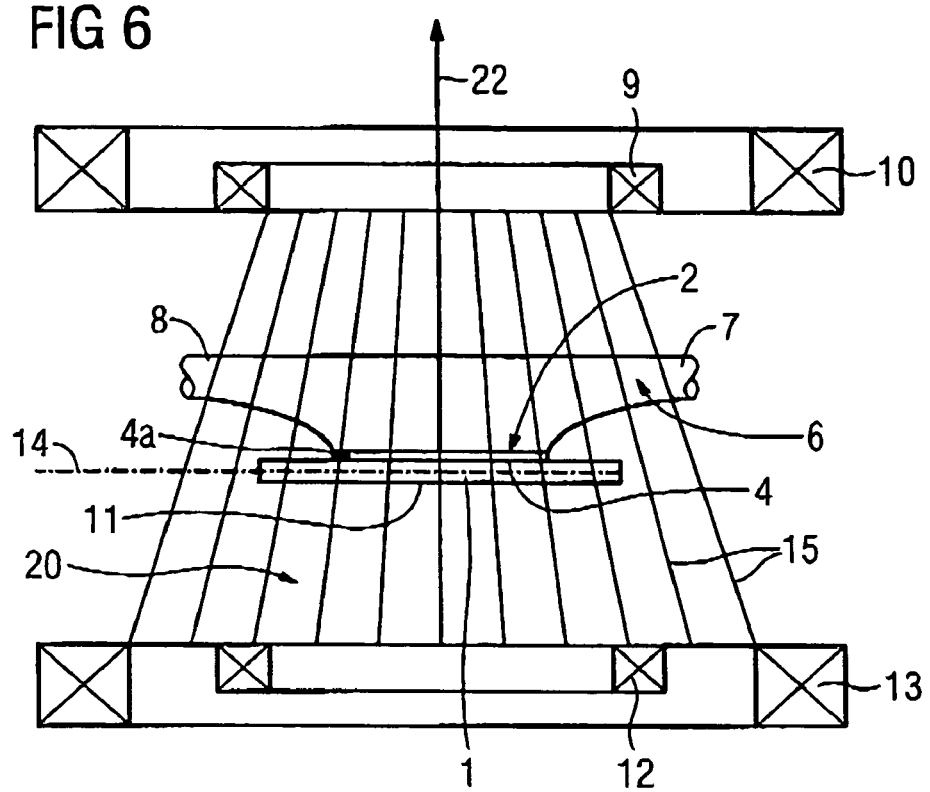
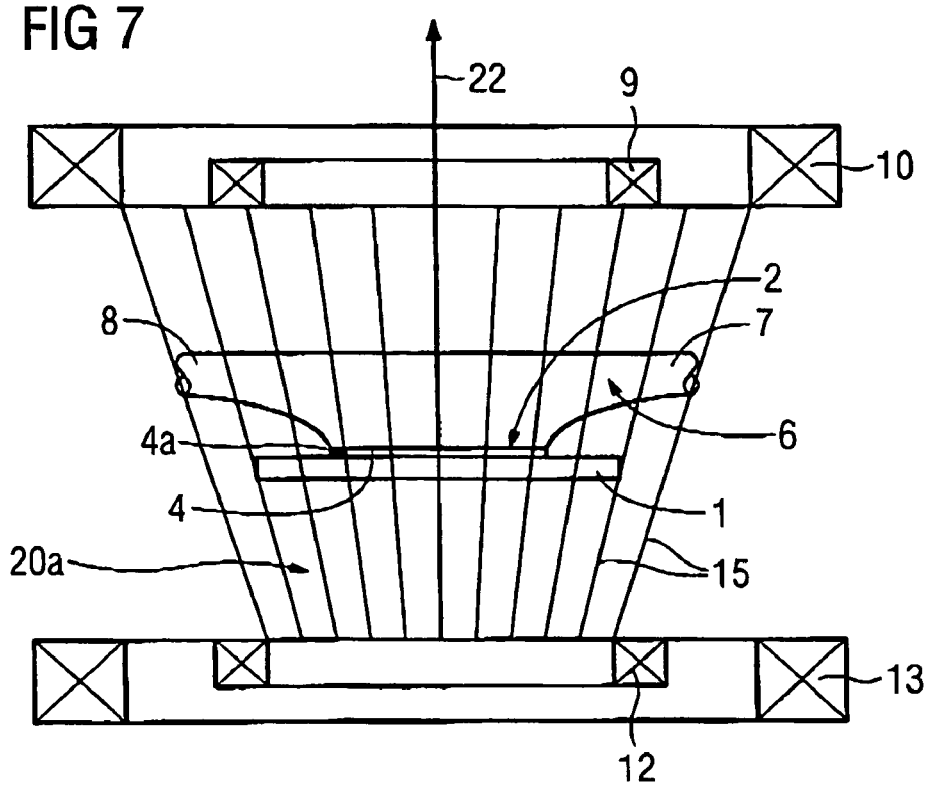

APPARATUS FOR CARRYING OUT AN ANALYSIS PROCESS, IN PARTICULAR FOR IDENTIFICATION OF BIOCHEMICAL MOLECULES, AND ANALYSIS PROCESSES WHICH CAN BE CARRIED OUT USING THIS APPARATUS

PRIORITY STATEMENT

The present application hereby claims priority under 35 U.S.C. §119 on German patent application number DE 10 2005 038 239.8 filed Aug. 12, 2005.

FIELD

The invention generally relates to an apparatus for carrying out an analysis process, in particular for identification of biochemical molecules or structures. The invention also generally relates to analysis processes which can be carried out using this apparatus.

BACKGROUND

The general aim in particular of biochemical analysis processes is to identify biochemical molecules, for example DNA sequences, proteins, haptenes and antigens. By way of example, probe molecules which are immobilized on a substrate within an analysis area are brought into contact with an analyte solution which contains the biochemical molecules or structures which have been mentioned (referred to for short in the following text as target molecules). Target molecules which match one another on the basis of the lock-and-key principle are, for example, bonded to a probe molecule forming bonded pairs of probe molecules. The occurrence of such reaction events is detected, for example optically or electrically, with the aid of labels or markers which are provided on the target molecules.

In addition to markers which can be detected in this way, magnetic marker particles are also used. In these cases, a homogeneous magnetic field acting on the analysis area is produced, and stray fields caused by the magnetic marker particles are detected with the aid of electromagnetic sensors. The literature publication "Biosensor based on force microscope technology" from J. Vac. Sci. Technology B 14(2), March/April 1996, P. 789 pp. describes a biosensor, in which mechanical oscillating bars, that is to say commercial piezo-electric scanning probe measurement tips are used for detection of magnetically induced forces. After a biological reaction, in particular for DNA identification, magnetic markers are left behind on the oscillating bar, and the change in the oscillation response to a variable magnetic force is used as a measure of the number of magnetic markers, and thus of the biological reaction. The magnetic field is produced by permanent magnets and a Helmholtz coil pair. Sensitive measurements in a liquid medium are not possible by means of oscillating bars.

U.S. Pat. No. 5,981,297 A describes the detection of selectively deposited molecules with magnetic markers by means of GMR sensors. The sensors can be used to obtain information about the concentration of the target molecules. In this case, it should be noted that there are no further-reaching analyses or means for carrying out the removal of markers which have not been bonded by means of a magnetic force. U.S. Pat. No. 6,180,418 B1 describes arrangements of moving permanent magnets by means of which magnetic markers (so-called beads) are moved during the course of an assay process. The beads are detected optically. Unbonded beads are removed by the application of a previously calculated force gradient, that is to say mechanical movement of the magnets. The biological bonding forces are not determined. Furthermore WO 00/61803 A1 describes a process using a cleaning step with magnetic forces. However, it is not possible to determine the biological bonding forces beyond the cleaning force of lpN, in this case. The detection and manipulation of biomolecules with magnetic particles (magnetic beads) are known from US 2004/0219695 A1. Magnets are moved backwards and forwards for this purpose.

U.S. Pat. No. 5,445,970 A describes a manually controlled balance of chemical and magnetic forces. The beads are detected optically. Little attention is paid to the magnetic design, and standard versions appear to be adequate. A GMI sensor for detection of magnetic markers is described in WO 02/29430 A1. In this case, the external magnetic field must have a constant magnitude in order to allow the GMI effect to be used. Bonding forces therefore cannot be determined. In this case, the beads are detected optically. Manipulators operating using magnetic beads are likewise known from DE 100 50 029 A1.

Finally, US 2005/0087000 A1 discloses a process, major parts of which are equivalent to the BARC sensor from U.S. Pat. No. 5,981,297A. The difference is the use of considerably smaller beads, which result in better measurement sensitivity. GMR sensors, in particular, are used to measure the density per unit area of the beads and to measure very small magnetic-field changes. Magnetic fields are produced by a coil pair.

SUMMARY

In contrast, an object of at least one embodiment of the invention is to further develop an apparatus such that it carries out further functions in addition to the reading of reaction events. These further functions may, in particular, and individually or in a combined form, be:
  a cleaning step by use of a magnetic field and application of a rinsing fluid for non-specific adhesions,
  a cleaning step by use of a magnetic field and application of a rinsing fluid for non-specific DNA bonds.

A further aim of at least one embodiment of the invention is to specify biochemical analysis processes which can be carried out using the new apparatus.

The subject matter of at least one embodiment of the invention is an apparatus which, in conjunction with a flow cell for an analyte solution and a substrate with an analysis area, has suitable device(s) for fluid open-loop and closed-loop control, for production and control of suitable magnetic fields, and for detection and evaluation of measurement values from the magnetic sensors. In this case, values for bonding forces relating to reaction events can be output, in particular, as evaluation variables. This can be used in particular in biochemical analysis processes, or else for other analysis processes with molecular reactions.

One major feature of at least one embodiment of the invention is that the apparatus has magnet device(s) for the production of, in particular, an inhomogeneous magnetic field acting in the analysis area, as well as suitable sequence control, as well. The magnet device(s) preferably include a first coil pair which is formed from two axially separated coils which are arranged with their turn planes approximately parallel to the flat plane of the analysis area and enclose the substrate between them, with the coil which is arranged on the analysis side of the substrate having a smaller diameter than the other coil. The field strength of a magnetic field which is produced in this way is inhomogeneous, for example anisotropic. In this case, the field strength increases, for example, in the direction of the normal to the analysis area—which runs essentially on a flat plane.

A second concentric coil pair is preferably provided in order to produce an inhomogeneous magnetic field in the opposite direction and is designed and arranged in the same way as the first coil pair, but with the coil having the larger diameter being arranged on the analysis side of the substrate. Two coil pairs arranged in a mirror-image form are advantageously used for the apparatus according to the invention. The respective upper and lower coils can be combined to form two coil systems.

An arrangement such as this also makes it possible, in particular, to produce a homogeneous magnetic field by driving or passing current through the two large and/or the two small coils, which can be done individually or at the same time. The axially symmetrical inhomogeneous or homogeneous fields produced in this way can be switched over quickly and can thus be used as accurately predeterminable magnetic forces for determination of formation forces in molecules.

One alternative refinement of the magnet device(s) for production of homogeneous and inhomogeneous magnetic-field distributions includes elongated coils, preferably similar to a rectangle. These are arranged in a comparable manner to the concentric coils to form pairs: a relatively small coil is in each case located opposite a larger one, and thus forms a coil pair with it. The magnetic field produced by one coil runs symmetrically with respect to the plane of symmetry, and is approximately homogeneous on the coil plane. It is thus homogeneous on a surface similar to a rectangle.

Located opposite this is a coil whose magnetic field is likewise a homogeneous rectangle, but with a considerably smaller narrow side. This results in a wedge-shaped magnetic-field profile. Coil systems are described by mirror-image formation and combination of the broader and of the narrower coil. Inhomogeneous wedge fields can be produced in different directions, as well as homogeneous fields, by joint connection of the broad and narrow coils.

In the apparatus according to at least one embodiment of the invention, at least one magnetic-field sensor for reading an analysis result is provided in the analysis area. The actual analysis area is arranged in a housing, which has an inlet-flow opening and an outlet-flow opening, for the analyte to be investigated.

In the processes which can be carried out using the apparatus according to at least one embodiment of the invention, provision is made for an inhomogeneous magnetic field to be applied to the analysis area before and/or after detection of reaction events. A magnetic field such as this causes a stray field which is distributed non-uniformly over the marker-particle extent. In consequence, a marker particle has a force applied to it acting in the direction of increasing field strength. This effect can be used in various ways, in particular in processes in which the intention is for target molecules to be bonded to probe molecules which have been immobilized in the analysis area.

In a first preferred process variant, an inhomogeneous magnetic field is produced in a cleaning step in such a manner that the marker particles are acted on by a force which removes them from the analysis area. This makes it possible, for example, for marker particles which have been absorbed on the surface of the analysis area or for non-coupled target molecules provided with marker particles to be removed from the analysis area. These are therefore not included in the detection process during a subsequent reading of bonding events, thus improving the validity and reproducibility of an analysis result.

For cleaning of an analysis area in the manner that has been mentioned, it is advantageous for the magnetic field to be aligned such that its field strength increases in the direction of the normal to the analysis area. This ensures that marker particles are effectively drawn upward out of the probe-molecule lawn without being severely impeded by probe molecules. The cleaning process is expediently supported by the application of a rinsing fluid.

In a cleaning step of the type mentioned, the strength of the magnetic field is chosen such that the force acting on a marked target molecule is less than the force which is required to separate a bond between the target molecule and the probe molecule in a coupled pair. This ensures that marker particles which are not coupled but in particular have been absorbed on the surface of the analysis area are removed, but the bond between the marked target molecule and the probe molecule in a coupled pair is not separated. The adsorption force of a marker particle in the area of the surface of the analysis area is about 1 to $\leq 10$ pN.

An appropriately configured inhomogeneous magnetic field allows marker particles to be removed with high reliability, without the bonded pairs being separated in the process. It is particularly expedient for the occupancy of the analysis area with marker particles to be determined before and after a cleaning step. If this does not change significantly before and after a cleaning step, then it can be assumed that there are no more marker particles which would corrupt the measurement result in the analysis area or on its surface.

In the case of bonding reactions between in particular biochemical molecules and structures, one problem that occurs is that a bonding or coupling event occurs not only when target molecules and probe molecules match one another 100%. Bonding can also occur with a lesser matching level. Such non-specific bonding events are also detected by previous analysis processes.

In order to allow a selection process to be carried out in this context, the magnetic-field strength in a further preferred process variant is chosen and set such that a marker particle which is coupled to a target molecule has a force applied to it which is sufficient in order to separate a specifically bonded or non-specifically bonded target molecule from a probe molecule. A process such as this can also be used for force spectroscopy purposes, in such a manner that the strength of the magnetic field is increased in steps, with the field strength of each step being chosen such that a force which is required to separate a particular specific or non-specific bond acts on a marker particle. A reading is in this case expediently carried out before and after a step increase in the field strength, with the result of this reading being governed by the number of respectively present bonded pairs. This allows a selection process to be carried out within non-specific bonding events on the basis of the bonding strength or on the basis of the degree of match between a target molecule and probe molecule, or allows a selection process to be carried out within specific bonding events on the basis of bonded pairs with different target molecules.

A further example embodiment variant provides for marker particles to be coupled to the target molecules only after the formation of bonded pairs. For example, in this case, the analysis area is supplied with an analyte solution with target molecules to which a coupling molecule is bonded, which can be coupled to a marker particle. Following the formation of bonded pairs, a solution containing marker particles is applied to the analysis area. This procedure is based on the discovery that the marker particles, which are considerably larger than the target molecules, restrict the mobility of the target molecules and thus impede or slow down their reaction with probe molecules. All of the process variants described here preferably use magnetite particles which are wrapped up in streptavidin and are coupled to the target molecule by biotin.

In a further process variant, an inhomogeneous magnetic field is produced while carrying out an analysis process, and its field strength increases in the opposite direction to the normal to the analysis area. Marker particles approach the surface of the analysis area, in a field such as this. If the analysis area is appropriately densely occupied by marker particles, they form an essentially closed layer, with a restricted sample volume with an increased reaction density being available between this layer and the surface of the analysis area.

BRIEF DESCRIPTION OF THE DRAWINGS

Further advantages and details of embodiments of the invention will become evident from the description of the figures, with reference to the attached drawing, and in conjunction with the patent claims, in which:

FIG. 5 shows the configuration of an apparatus which is suitable for carrying out a biochemical process, FIGS. 6, 7 show apparatuses corresponding to FIG. 5, which are suitable for production of an inhomogeneous magnetic field.

DETAILED DESCRIPTION OF THE EXAMPLE EMBODIMENTS

The aim is to provide an apparatus for carrying out an analysis process more easily, in which magnetic measurement processes and metrology are used. The aim of the process, in particular, is to determine bonding forces in reaction events by use of magnetic forces.

One particular aim of the apparatus, however, is to carry out biochemical analysis processes in order to identify biochemical molecules or structures in an analyte solution. In this case, in addition to the fluid control, as is normal in biochemistry, for the analyte solution, a particular role is also played by the production of magnetic fields acting in the analysis area, the magnetic-field control and/or magnetic-field measurement with common sequence control, as well as the detection and evaluation of the measurement values.

Figure 1:
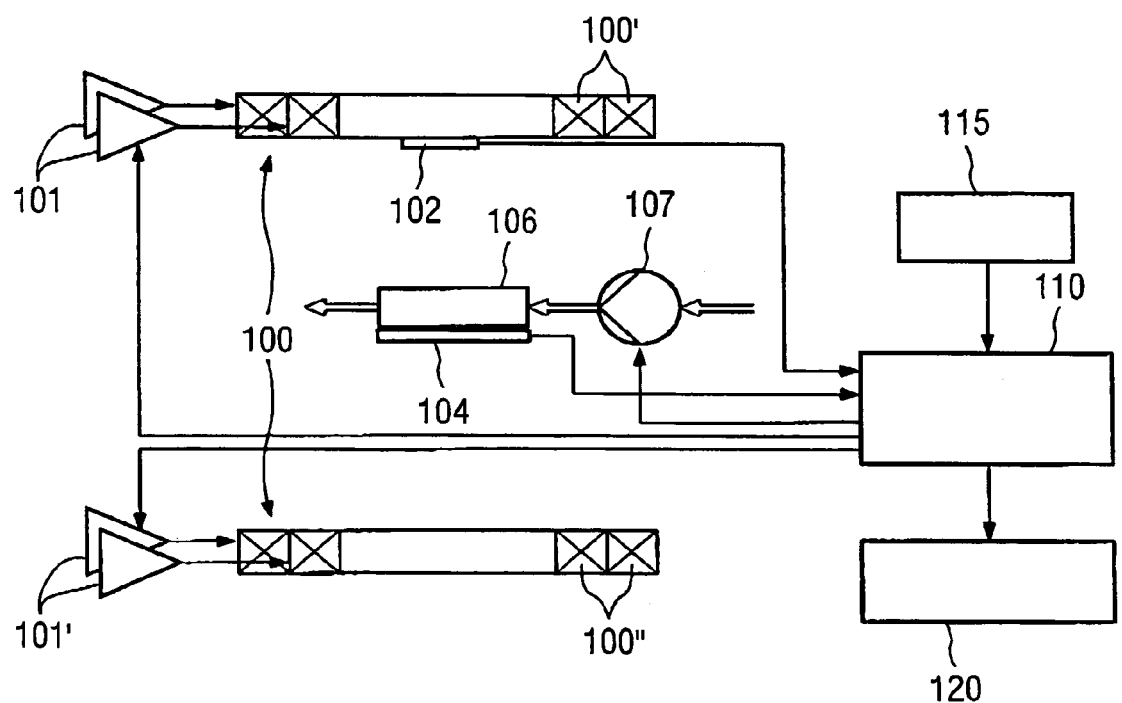
FIG. 1 shows a block diagram of an apparatus according to an embodiment of the invention, suitable for magnetic measurements in a flow cell.

In FIG. 1, a device for magnetic-field production is denoted by 100, and has an associated control device 101 or 101' as well as control electronics 110 as sequence control. 102 denotes a magnetic-field sensor for measurement of the magnetic field.

At least two coils 100' or 100" of a different type are used as the device for magnetic-field production, so that at least one inhomogeneous magnetic field can be produced. This will be described in detail further below.

A flow cell 106 with a pump 107 for an analyte has an analysis area which has an associated high-resolution sensor for very small magnetic-field changes.

The measurement signals for the magnetic field and the magnetic-field changes produced in the analysis area 104 are passed to an evaluation unit 110. The evaluation process is carried out conformally with respect to the sequence control in the evaluation unit 110, corresponding to an input predetermined in the unit 115, with the results being recorded in an output unit 120.

In particular, inhomogeneous magnetic fields are required for the analysis processes to be carried out. Fields such as these can be produced either as a conical field or as a wedge-shaped field, as is illustrated in FIG. 2.

Figure 2:
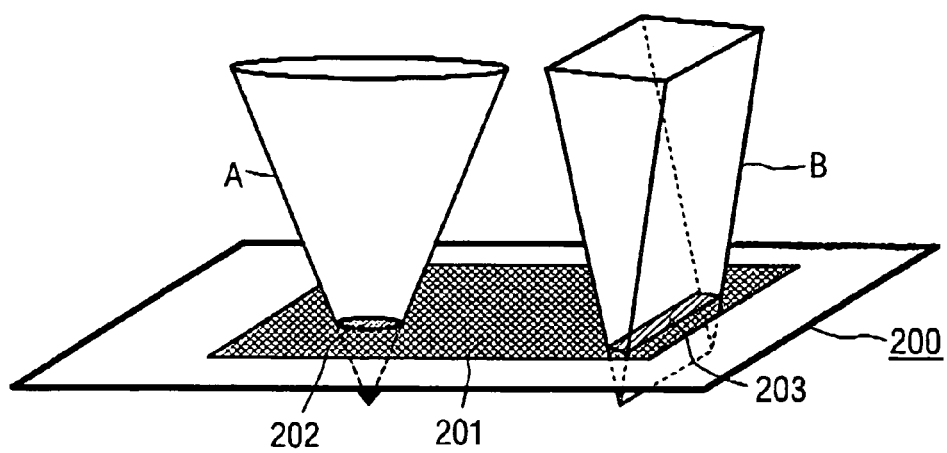
FIG. 2 shows the principle for production of inhomogeneous magnetic fields (wedge/cone)

In FIG. 2, 200 refers to a wafer on whose measurement surface 201 a sensor is intended to be formed. The conical field is annotated A, and the wedge-shaped field is annotated B. Thus, in the first case, a cylindrical or axially symmetrical analysis field 202 is produced on the plane of the measurement surface 201 of the wafer 200 (so-called layer plane), and in the second case a rectangular analysis field 203, which is symmetrical with respect to the plane, is produced.

In the case of axially symmetrical magnetic-field arrangements, the homogeneity is very good in the area of the central axis. For analysis areas which are very much smaller that the diameter of the smaller coil a homogeneous field can be assumed only with very low field components on the chip plane. Concentric coils are simple to manufacture.

The approximately rectangular field has advantages in analysis areas which are similar to the coil dimensions. Rectangular dimensions are the rule in flow cells. For space reasons, a small, rectangularly matched coil arrangement may be required in practice, whose homogeneity over the chip is better than would be the case with an axially symmetrical magnetic-field arrangement of the same size.

Figure 3:
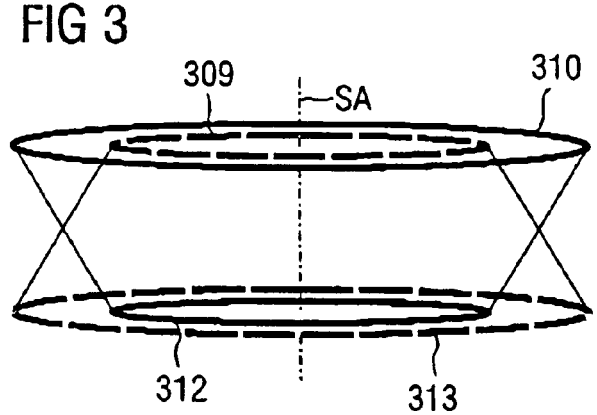
FIG. 3 shows a coil pair/system with circular coils.

FIG. 3 shows, for a practical implementation, that, in the case of an arrangement including coils arranged at a distance from one another, two respective coils 309, 310 and 312, 313 which are concentric on a plane in each case form a coil system, and two non-identical coils 309, 312 and 310, 312 which are located on different planes in each case form a coil pair. With an arrangement such as this, when one coil pair is driven, inhomogeneous magnetic fields can be generated with different gradients. It is also possible to produce homogeneous magnetic fields by driving coils of the same size.

The principle of a coil pair/coil system makes it possible to produce suitable magnetic fields in a simple manner in the analysis area of the flow cell, with this being referred to in the following text as so-called magnetic-field device(s). This simple arrangement allows any desired homogeneous and inhomogeneous fields to be produced with field changes in the microsecond region, by in each case selectively driving or passing current through the suitable coils, and this can be done individually or all at the same time.

These device(s) thus include a first coil pair which is formed from two axially separated coils (axially separated along axis SA or axis SE) which are arranged with their turn planes approximately parallel to the flat plane of the analysis area and enclose the substrate between them, with the coil which is arranged on the analysis side of the substrate having a smaller diameter than the other coil. The field strength of a magnetic field that is produced in this way is anisotropic. This increases in the direction of the normal to the analysis area— which runs essentially on a flat plane. A second coil pair is preferably provided in order to produce a magnetic field in the opposite direction, and is designed and arranged in the same way as the first coil pair, but with the coil having the larger diameter being arranged on the analysis side of the substrate. This thus results in two coil pairs which are arranged in mirror-image form. The respective upper and lower coils can be combined to form two coil systems.

Figure 4:
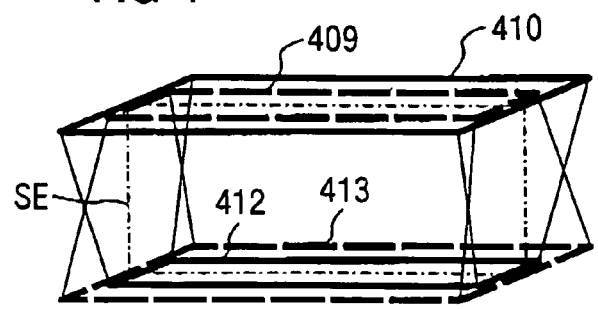
FIG. 4 shows a coil pair/system with rectangular coils.

One alternative refinement of the magnet device(s) for production of homogeneous and inhomogeneous magnetic-field distributions comprises elongated coils 409, 410, 412, 413, preferably similar to a rectangle, as is illustrated in FIG. 4. The coils 409, 410, 412, 413 are arranged in a comparable manner to the concentric coils 309, 310, 312, 313 from FIG. 3 to form pairs. One relatively small coil is in each case opposite a larger one, and forms a coil pair with it. The magnetic field which is produced by one coil is approximately homogeneous on the coil plane, that is to say it is homogeneous on a surface similar to a rectangle.

A coil whose magnetic field is likewise a homogeneous rectangle, but with a considerably smaller narrow side, is located opposite it. This results in a wedge-shaped magnetic-field profile. Coil systems are described by mirror-imaging and combination of the broader and narrower coil. Inhomogeneous wedge-shaped fields can be produced in different directions, or else homogeneous fields, by way of joint connection of the broad and narrow coils.

In order to read an analysis result, at least one magnetic-field sensor is provided in the analysis area. Furthermore, the analysis area is arranged in a housing which has an inlet-flow opening and an outlet-flow opening. The apparatus thus contains device(s) for fluidic open-loop and/or closed-loop control, for generation and control of suitable magnetic fields, for reading magnetic sensors and/or for storage and processing of states which have been read from the magnetic sensors and for detection and evaluation of measurement values. The magnetic fields are thus correlated with the bonding forces for this specific purpose.

Device(s) containing statistics software may be provided for assessment of the states and changes to the states. The stated device(s) are formed by at least one controller or microcontroller with associated software.

This thus results in specific sequences for different analysis processes, and these can be illustrated by means of flowcharts. In general, by way of example the sequence control for measurement of the bonding strength is:
a) START
b) Pump analyte solution
c) Apply a defined homogeneous magnetic field by driving the coils, with possible readjustment on the basis of the measured magnetic-field strength
d) Measure the marker-particle occupancy in the analysis area, and output the results
e) End signal reached, for example no more marker particles found
f) Apply a defined inhomogeneous magnetic field (washing field), test the bonding force of reaction events by means of magnetic forces
e) Repeat from step b) or from step c) as far as the signal for the end
f) END Sequence control such as this can be carried out in various ways, for example by an operator or by way of a switching matrix. It is advantageous to use a microcontroller with appropriate software. In addition to the measurement of the bonding strength, the software can carry out further tasks and/or the abovementioned sequence items in an improved manner:
soft fluidics start and stop characteristic
control, connection and disconnection of the magnetic field without overshoots (active compensation for the inductive behavior of the coils)
provision of a database with reference values
deconvolution of the influence of the magnetic-field distribution, which is not ideally homogeneous, for better determination of the marker positions
more exact determination of the marker occupancy through the use of software statistics modules for marker occupancy on a sensor, for example taking into account different positions of the marker relative to the areas of the sensor with different sensitivity, or in a sensor array, for example averaging of a plurality of sensors
calculation of the effective force in Newtons from the measured inhomogeneous magnetic-field strength in T (or H)
storage of all the recorded data for subsequent evaluation
automatic calculation of so-called fit parameters for the evaluation
in addition: graphical display of the marker occupancy as a function of the applied forces The stated items are significant and indicate the basic idea of software control for an existing microcontroller, and of the program structure that is used for this purpose. Further items, for example temperature control, are possible.

A first example is a cleaning step by use of a magnetic field and application of a rinsing fluid for non-specific adhesions. In this case:
a) START
b) Pump the analyte solution
c) Apply a defined homogeneous magnetic field and measure the marker-particle occupancy, and output the results
d) Apply a defined inhomogeneous magnetic field (washing field)
  Marker particles with non-specific adhesions are removed by magnetic forces
e) Pump a rinsing fluid
f) Apply a defined homogeneous magnetic field and measure the marker-particle occupancy, and output the results
g) END A second example is a cleaning step by use of a magnetic field and application of a rising fluid for non-specific DNA bonds. In this case:
a) START
b) Pump the analyte solution
c) Apply a defined homogeneous magnetic field and measure the marker-particle occupancy, and output the results
d) Apply a defined inhomogeneous magnetic field of a first, low strength (washing field)
  Marker particles with non-specific adhesions are removed by magnetic forces
e) Pump a rinsing fluid
f) Apply a defined homogeneous magnetic field and measure the marker-particle occupancy, and output the results
g) Apply a defined inhomogeneous magnetic field of a second, greater strength than the washing field (attempt to separate short sequences of AT pairs and CG pairs:

so-called separating field). In this case, marker particles are removed from non-specific DNA bonds by magnetic forces h) Repeat steps from e) until the signal for End is produced, since for example, no more marker particles are found i) END The device(s) provided for magnetic-field control and measurement allow the deliberate use of magnetic fields as force source, preferably in a direction at right angles to the analysis area. In a first application, adhesively bonded magnetic marker particles are removed by a magnetic field of a first strength, which is still low. This is referred to as (stringent) washing.

Remaining markers are bonded with stronger mechanisms in the analysis area, although these bonding forces are also finite. It is particularly interesting to analyze these forces since they allow the type of bonding to be deduced. By way of example, DNA chains of different length exhibit a bonding force which can be calculated. This can be used, for example, in the course of biochemical investigations for SNP analysis.

Successively increasing inhomogeneous magnetic fields (and the forces associated with them) are then applied following the washing step, and the marker occupancy is in each case determined. If beads are removed in this way, an adequate force has in consequence been exerted, and the bond is separated. A sequence of applied separating fields with the marker occupancy varying thus represents a type of force spectroscopy on the effective bonding forces.

The apparatus used to carry out an analysis process in practical trials comprises, as is shown in FIG. 5, a substrate 1 approximately in the form of a plate. An analysis area 2 is defined on one flat face of the substrate 1, on which probe molecules 19 (see FIG. 8) are immobilized. The analysis area 2 is covered by a sensor layer 4 which contains at least one magnetic-field sensor 4a.

It is also possible for the analysis area to be formed by an array (e.g., an one-dimensional array or a two-dimensional array) including a large number of analysis positions, with each analysis position being associated with one magnetic-field sensor $4_a$. By way of example Hall sensors or magento-resistive (XMR) sensors, in particular anisotropic magneto-resistive (AMR), giant magneto-resistive (GMR) and tunnel magneto-resistive (TMR) sensors, may be used as the sensors. The latter are based on different magneto-resistance effects which occur in layer systems with very thin layers.

Figure 8:
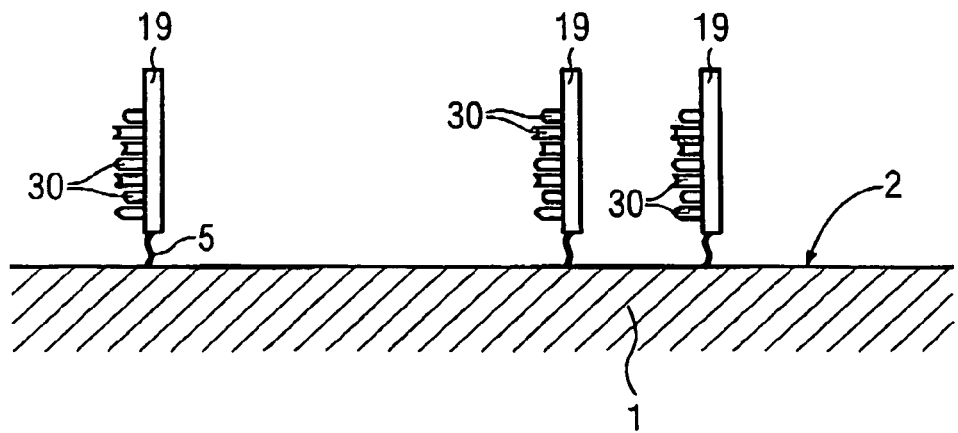
FIGS. 8, 9 show schematic illustrations of a first biochemical analysis process which can be carried out using the apparatus according to an embodiment of the invention.
Figure 9:
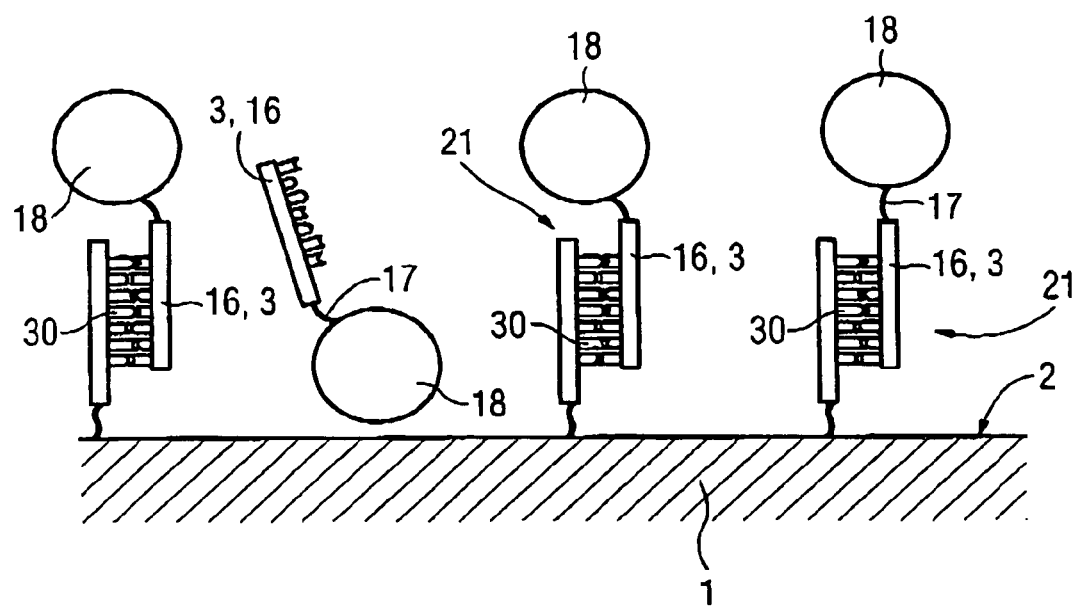

As can be seen from the outline sketch shown in FIG. 8, probe molecules 19, for example DNA oligomers, are bonded with the aid of a spacer 5 to the surface of the sensor layer 4 in a known manner, which will not be described in detail here. Different covalent, ionic or similar types of bonding are possible, for example gold-thiofurane bonds. The analysis area 2 is surrounded in a fluid-tight manner by a housing 6 which has an inlet-flow opening 7 and an outlet-flow opening 8. Two magnet coils 9, 10 are provided at a distance from the analysis area 2, and two further magnet coils 12, 13 are provided at a distance from the rear face 11 of the substrate 1. The turn planes of the coils 9, 10, 12, 13 run parallel to the flat plane 14 of the analysis area 2 or of the substrate 1, with one coil 10, 13 of the two coils which are associated with one face of the substrate 2 in each case having a larger diameter, and concentrically surrounding the smaller coil 9, 12 in each case. The larger coils 10, 13 also have a greater number of turns than the smaller coils 9, 12 surrounded by them.

The coils 9, 10, 12, 13 can be driven in pairs via a control device, which has already been explained with reference to FIGS. 1 as well as 5 to 7, in order to produce the magnetic field. A homogeneous magnetic field, for example for detection of the occupancy of the analysis area 2 with marker particles, can be produced when either the smaller coils 9, 12 or the larger coils 10, 13 together form a Helmholtz coil pair.

If, in contrast, the aim is to produce an inhomogeneous magnetic field, that coil 9 which is arranged above the substrate and above the housing 6 in FIG. 5 is connected to the larger coil 13 positioned underneath the substrate 1, and the smaller coil 12 which is surrounded by it is connected to the larger coil 10 arranged above the substrate 1, to form a coil pair. As is indicated in FIGS. 2 and 3, the coil pair 9/13 produces a magnetic field 20 whose field strength increases from the coil 13 toward the coil 9, and in the direction of the normal 22 to the analysis area. A magnetic field 20a with the opposite characteristics is achieved by combining the coil 12 with the coil 10 to form a coil pair (FIG. 7).

The field strength (which increases in one direction) of the magnetic field 20, 20a is indicated by converging field lines 15 in FIG. 6 and FIG. 7. This preferably results in the magnetic field having a linear gradient in each case.

In the arrangement shown in FIGS. 6 and 7, inhomogeneous magnetic fields can be produced in a plurality of directions. The inhomogeneity can be set by appropriate coil geometries or yoke geometries. As can be seen from FIG. 2, conical (axially symmetrical) or wedge-shaped (area-symmetrical) field profiles can be used, as is illustrated, in each case schematically, in the figures.

Following the above description of the novel apparatus, specific applications will now be described. The process of operation of one specific process will be explained in more detail with reference to a first process variant.

One frequent analysis object is to identify DNA oligomers 16 with a specific base sequence as target molecules 3. The DNA oligomers 16 are, by way of example, sections of longer DNA strands, which have been cut out from them using known methods. Coupling molecules 17 are bonded covalently to the DNA oligomers 16, and can be coupled to correspondingly prepared marker particles or beads 18. Beads are particles with a diameter of a few hundred nanometers, which are magnetized only slightly, or not at all, in the absence of an external magnetic field.

By way of example, these are particles composed completely of magnetite. However, the beads 18 may also contain a plastic matrix in which magnetite is incorporated. They are provided with a coating to which a coupling molecule is coupled. In the past, this has been achieved primarily by coating the beads with streptavidin which forms a fixed covalent bond with biotin as a coupling molecule.

Probe molecules 19 are immobilized by spacers 5, which have already been mentioned in the introduction, on the analysis area 2 (preferably formed by a flat surface) and on the surface of the sensor layer 4. The probe molecules 19 are, for example, synthetically produced DNA molecules which have precisely the sought sequence of bases 30. An analyte solution which contains the DNA oligomers 16 as mentioned above as target molecules is supplied to the analysis area 2 via the inlet-flow opening 7 on the housing 6.

A pump system which has a closed-loop and open-loop control device is used for this purpose, as has been described in detail with reference to FIG. 1 and as is known from biochemical metrology.

DNA oligomers whose base sequence at least partially matches that of the probe molecules 19 are bonded to the probe molecules 19 in a so-called hybridization reaction.

Before taking a reading of the occupancy of the analysis area 2 with beads 18, an inhomogeneous magnetic field 20 (see FIG. 6) is produced by passing current through the coil pair 9/13, and the field strength of this magnetic field 20 increases in the direction of the normal 22 to the analysis area 2. The stray field which is produced on the beads 18 as a result of the inhomogeneous magnetic field 20 is distributed unequally with respect to the circumferential area of a bead 18, in such a manner that this results in a force acting in the direction of the normal 22. The strength of the inhomogeneous magnetic field 20 is chosen such that a force acts on the bead 18 which is bonded to a DNA oligomer 16, with this force being less than the force which is required to separate a bond between the DNA oligomer 16 and the probe molecule 19 of a bonded pair 21. The adsorption force of coated beads 18 in the region of the surface of the analysis area 2 is in the order of magnitude of >1 pN, while in contrast the bonding forces between target molecules and probe molecules are in the region of at least 100 pN.

Thus, if the inhomogeneous magnetic field 20 is chosen so as to ensure a force of about 70 pN on the beads 18, only marked DNA oligomers 16 or else individual beads 18 which are not coupled to a DNA oligomer 16 are removed from the analysis area 2, without bonded pairs 21 being separated in the process. In order to monitor the success of a cleaning step, the occupancy of the analysis area 2 with beads 18 is detected before and after this step. If there is no significant difference between the occupancy before and after a cleaning step, then it can be assumed that the detected bead occupancy is caused exclusively by bonded pairs 21.

A conventional controller is used to detect the bead occupancy of the analysis area 2 and to form the difference between two occupancy states, for example the occupancy before and after a cleaning step. This also allows the use of statistics software for assessment of movement states and their changes.

Figure 10:
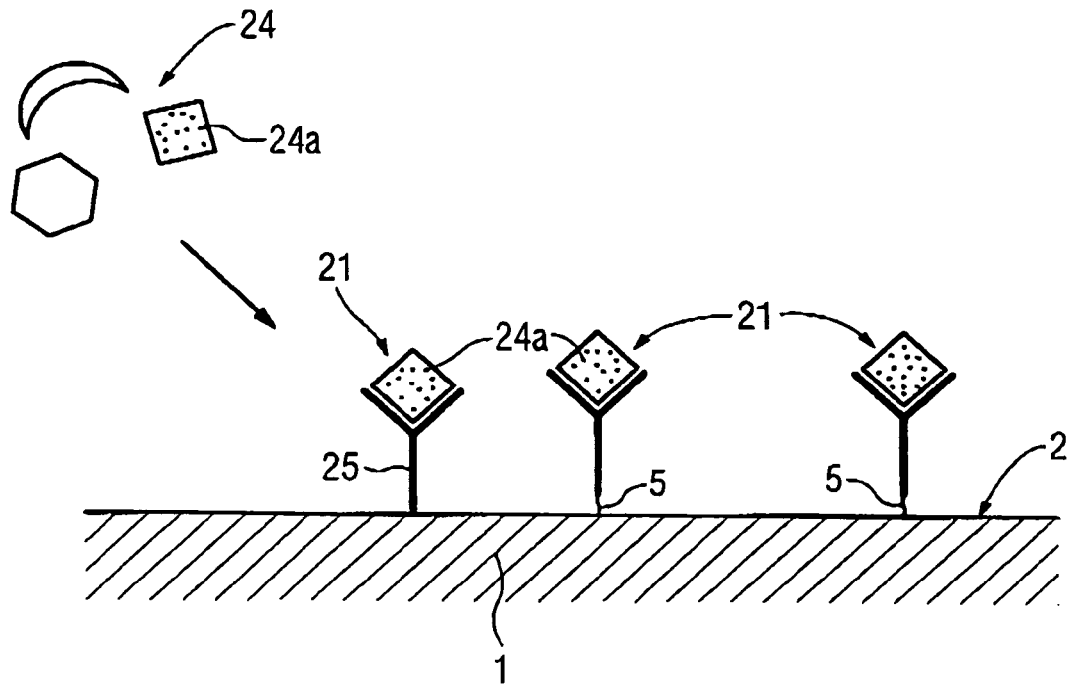
FIGS. 10, 11 show schematic illustrations of one variant of the analysis process shown in FIGS. 8/9.
Figure 11:
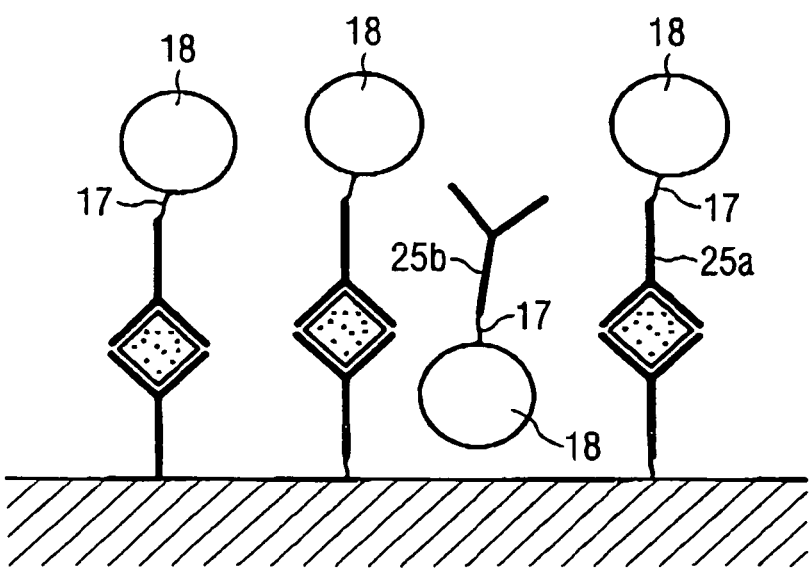
Figure 12:
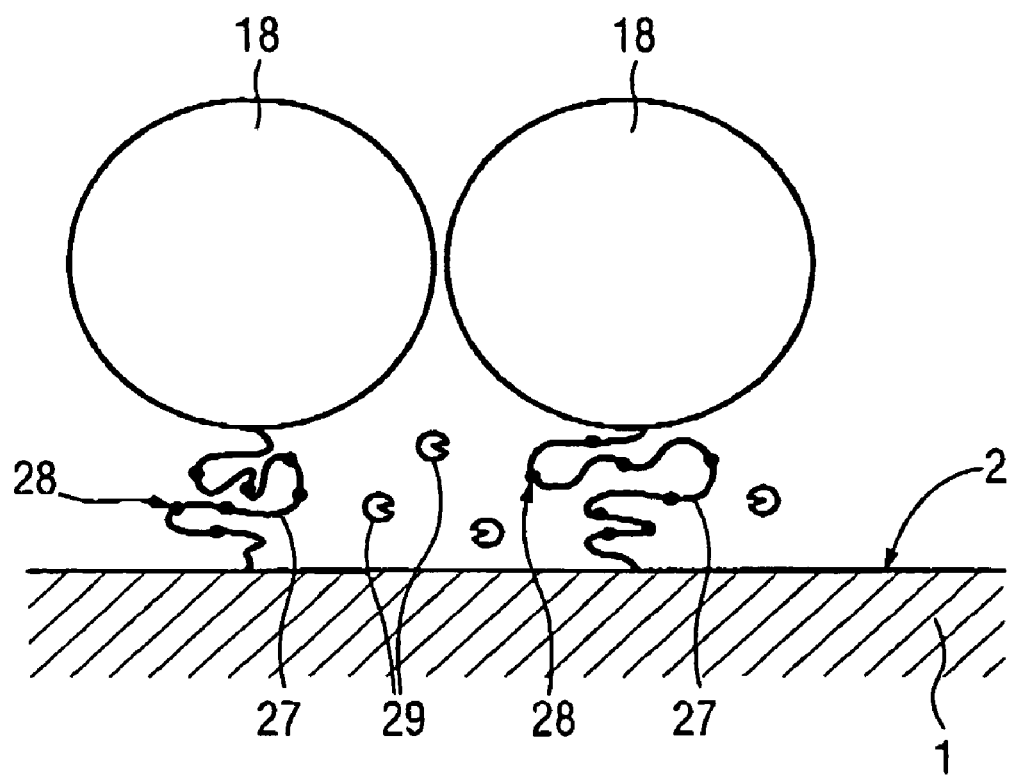
FIG. 12 shows a schematic illustration of a further variant of the analysis process shown in FIGS. 8/9.

FIGS. 10 and 11 illustrate a second process example. This relates to the search for specific antigens in analyte solutions. Antibodies 25 are once again immobilized on the analysis area 2 via a spacer 5. The housing 6 is fed with an analyte solution containing antigens 24, by its inlet-flow opening 7. Antigens 24a which fit the antibodies 25 accumulate on them, forming bonded pairs 21. After rinsing of the analysis area 2 with a cleaning solution, for example with distilled water, the housing 6 is fed with a solution which contains antigens 25a, which correspond to the immobilized antigens 25 and are marked with beads 18. The antibodies 25a accumulate on the antigen 24a of a bonded pair 21. The bonded pairs 21 can now be detected with the aid of a homogeneous magnetic field, and by use of magnetic-field sensors. In this case as well, it may be expedient to remove unbonded marked antibodies 25b with the aid of an inhomogeneous magnetic field 20, as has already been described further above, in a cleaning step, and thus to improve the detection validity, particularly in quantitative terms.

In many biochemical reactions which are based on the lock-and-key principle, for example antibody-antigen reactions or the hybridization of DNA sequences, bonding takes place even if the match between the bonding-relevant areas of the bonding partners is not 100%. Non-specific bonds such as these are frequently undesirable. In a further preferred process variant, a selection process can be carried out on the basis of bonding quality, in which an inhomogeneous magnetic field is produced before an analysis result is read, and its field strength is chosen such that the beads 18 in coupled pairs 21 have a force applied to them in the direction of the normal 22 which is less than the force required to separate a specific bond between a target molecule and a probe molecule.

In the case of hybridization of a DNA oligomer 16 with a probe molecule 19 using a complementary base frequency, bonded pairs 21 such as these can thus be detected in which the mutual base sequences differ from one another. The bonding forces between two complementary base pairs (adenine-thymine, cytosine-guanine) are known, so that the force which is required to "tear off" a non-specific bond can be calculated. All of the target molecules which are below a predetermined degree of match can thus be removed from the analysis area 2 by application of an inhomogeneous magnetic field which produces a corresponding tearing-off force.

By detection of the bead occupancy before and after a selection step such as this, it is possible to determine whether all of the bonds with a predetermined degree of match have been separated. Furthermore, it is possible to make a quantitative statement on the proportion of the non-specifically bonded target molecules which have in each case been removed, in comparison to specifically bonded target molecules. A further refinement of this process variant provides for the field strength of the inhomogeneous magnetic field to be increased in steps, with the field strength of a step being chosen such that the force which is required to separate one particular non-specific bond acts on each of the marker particles.

This allows a type of spectroscopy to be used to determine whether particular non-specific bonds are present, and if appropriate, the proportion of them.

In a further process variant, an inhomogeneous magnetic field whose field strength increases in the opposite direction to the normal 22 to the analysis area 2 is produced while carrying out an analysis process. With a magnetic field such as this, a force which approaches the analysis area 2 acts on a bead 18. This creates a suspended sample volume 26 between the beads 18 and the analysis area 2.

The latter can be used usefully, for example, in the following process example: in order to determine the splitting specificity of a protease, polypeptides 27 which have each been marked with a bead 18 are immobilized on the surface of the analysis area 2. These have a large number of possible splitting points 28, at which a protease 29 can act. Since the beads 18 are moved toward the surface of the analysis area 2 with the aid of an inhomogeneous magnetic field 20a (see FIG. 7), a constricted sample volume 26 is formed. The concentration of proteases in this sample volume 26 is, however, the same as that in the remaining volume of the housing 6. The process of the beads 18 approaching the surface of the analysis area 2 results in the polypeptides 27 being compressed, with a large number of loops being formed. The splitting points, which previously have been distributed over a relatively large volume, are now arranged in the smaller sample volume, and this corresponds to an increased concentration of splitting points 28, and reaction density. In a corresponding manner, a protease 29 finds a suitable splitting point 28 more quickly because of the greater number on offer.

In order to evaluate the analysis result, an inhomogeneous magnetic field is produced as shown in FIG. 6 or FIG. 7, the beads 18 of separated polypeptides 27 being removed from the analysis area 2, and being removed from the housing 6 by a rinsing process. In this process variant as well, it may be expedient to carry out a cleaning step, using a magnetic field 20 as shown in FIG. 6, prior to the detection process.

In particular, biochemical analysis processes have been described with reference to FIGS. 8 to 12. The apparatus according to an embodiment of the invention can be used just as well for general analysis purposes, as well. It is particularly advantageous that the nature and strength of the magnetic field in the normal direction to the analysis area can be predetermined as required. This in its own right results in application options for the apparatus according to an embodiment of the invention, in which bonding forces can be determined by use of externally applied forces.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. An apparatus for carrying out an analysis process wherein probe molecules, immobilized on a substrate within an analysis area, are brought into contact with an analyte solution which contains target molecules as reaction partners, reaction events are detected between the target molecules and the probe molecules with the aid of magnetic marker particles coupled to at least one of the target molecules and the probe molecules, and a bonding force of the reaction events is determined by magnetic fields generated by the magnetic marker particles, the apparatus comprising:
a flow cell including the analyte solution;
a substrate within the flow cell including the analysis area and the probe molecules immobilized in the analysis area;
sensors for magnetic-field measurement, the sensors being sensitive to the magnetic fields generated by the magnetic marker particles;
first means for at least one of fluidic open-loop and closed-loop control;
second means for production of at least an inhomogeneous magnetic field acting at least at times in the analysis area and for the removal of unbound magnetic marker particles coupled to target molecules from the analysis area using the at least one inhomogeneous magnetic field, the second means including a first coil pair formed from two axially separated coils having different diameters;
third means for magnetic-field control of the sensors for magnetic-field measurement;
fourth means for detection and evaluation of measurement values; and
fifth means for correlation of the magnetic field generated by the magnetic marker particles and the bonding forces,
wherein the first to fifth means form sequence control for determination of the bonding forces of the reaction events,
wherein the two axially separated coils are arranged with their turn planes parallel to a flat plane of the analysis area and enclose the substrate between them, with one coil of the two axially separated coils arranged on an analysis side of the substrate and having a smaller diameter than the other coil of the two axially separated coils,
the second means includes a second coil pair designed and arranged in the same way as the first coil pair, but with one coil of the two axially separated coils being arranged on the analysis side of the substrate and having a larger diameter than the other coil of the two axially separated coils, and
the inhomogeneous magnetic field is produced by the one coil of the first coil pair having a different diameter than the other coil of the first coil pair, and the one coil of the second coil pair having a different diameter than the other coil of the second coil pair; and wherein the coils which are respectively associated with one side of the substrate are in the same plane.

2. The apparatus as claimed in claim 1, wherein the coils which are respectively associated with one side of the substrate are arranged concentrically with respect to one another.

3. The apparatus as claimed in claim 1, wherein the one coil having the larger diameter of the second coil pair and the one coil having the smaller diameter of the first coil pair are separately drivable in order to produce a homogeneous magnetic field.

4. The apparatus as claimed in claim 1, wherein the second means is equally suitable for generating, at least one of a homogeneous magnetic field and the inhomogeneous magnetic field, by suitable driving of the coils.

5. The apparatus as claimed in claim 1, wherein the magnetic field which is produced by the second means is symmetrical either with respect to an axis of the analysis area or with respect to a plane at a right angle to the analysis area of the substrate.

6. The apparatus as claimed in claim 1, wherein a measurement layer including at least one of the magnetic-field sensors is arranged in the analysis area.

7. The apparatus as claimed in claim 6, wherein a plurality of the magnetic-field sensors form a two-dimensional array.

8. The apparatus as claimed in claim 1, wherein the flow cell is formed together with the analysis area by a housing which includes an inlet-flow opening and an outlet-flow opening.

9. The apparatus as claimed in claim 1, wherein a Hall sensor is provided as a device for the magnetic-field measurement.

10. The apparatus as claimed in claim 1, wherein magneto-resistive (XMR) sensors are used as a device for the magnetic-field measurement.

11. The apparatus as claimed in claim 10, wherein the XMR sensors include at least one of anisotropic magneto-resistive (AMR), giant magneto-resistive (GMR) and tunnel magneto-resistive (TMR) sensors.

12. The apparatus as claimed in claim 11, wherein the XMR sensors form a one-dimensional or two-dimensional array, which covers a measurement field in the analysis area.

13. The apparatus as claimed in claim 1, wherein the means for detection and evaluation of measurement values is a device capable of reading the magnetic-field sensors and of storing states which have been read from the magnetic-field sensors.

14. The apparatus as claimed in claim 1, wherein the means for detection and evaluation of measurement values is equally suitable for assessment of the states which have been read from the magnetic-field sensors.

15. The apparatus as claimed in claim 14, wherein the means for detection and evaluation of measurement values is equally suitable for changing the states which have been read from the magnetic-field sensors.

16. The apparatus as claimed in claim 14, wherein the means for assessment of the states contains statistics software.

17. The apparatus as claimed in claim 1, wherein the means for detection and evaluation of the measurement values are formed by at least one controller or microcontroller, operable with statistics software.

18. The apparatus as claimed in claim 1, wherein the coils of the coil pairs include a circular cross section.

19. The apparatus as claimed in claim 1, wherein the coils of the coil pairs include a rectangular cross section.

* * * * *